(12) United States Patent
Mahaffey, Jr. et al.

(10) Patent No.: US 6,544,537 B1
(45) Date of Patent: Apr. 8, 2003

(54) OPACIFIED AQUEOUS COMPOSITION FOR TOILETS

(75) Inventors: Robert L. Mahaffey, Jr., Spartanburg, SC (US); Sandra C. Morse, Spartanburg, SC (US)

(73) Assignee: Milliken & Company, Spartanburg, SC (US)

( * ) Notice: Subject to any disclaimer, the term of this patent is extended or adjusted under 35 U.S.C. 154(b) by 0 days.

(21) Appl. No.: 08/503,294

(22) Filed: Jul. 17, 1995

(51) Int. Cl.$^7$ ............................................. A01N 25/02
(52) U.S. Cl. ..................... 424/405; 424/10.3; 424/76.7; 424/76.8; 424/76.9; 4/222; 4/223; 4/DIG. 10
(58) Field of Search ........................ 424/14, 405, 10.3, 424/76.7, 76.8, 76.9, 78.31–78.38, 543; 4/222, 223, 610; 19/161, 162

(56) References Cited

U.S. PATENT DOCUMENTS 3,723,326 A  3/1973 Cheng .................. 252/107
4,218,432 A * 8/1980 Watanabe et al. .............. 424/14
5,384,114 A * 1/1995 Dowell et al. ............. 424/70.1

FOREIGN PATENT DOCUMENTS

| EP | 0 013 043 | 7/1980 |
| EP | 0 144 958 | 6/1985 |
| EP | 0 498 667 | 8/1992 |
| EP | 0 562 637 | 9/1993 |
| GB | 1180917 | 2/1970 |
| WO | WO 82/01319 | 4/1982 |

OTHER PUBLICATIONS

Hawley's Condensed Chemical Dictionary, Richard J. Lewis Jr., pp. 853 and 917 Dec. 1993.*

* cited by examiner

Primary Examiner—Neil S. Levy
(74) Attorney, Agent, or Firm—Terry T. Moyer; Timothy J. Monahan

(57) ABSTRACT

A toilet system is provided having a receptacle, into which human waste is discharged, the receptacle contains an aqueous disinfectant composition which has an opacifier dispersed therein to reduce the light transmittance of the composition.

12 Claims, No Drawings

OPACIFIED AQUEOUS COMPOSITION FOR TOILETS

BACKGROUND OF THE INVENTION

This invention relates to an aqueous composition for toilets, which contains an opacifier to "conceal" accumulated waste.

Aqueous disinfectant compositions are often used in toilet receptacles for human waste, such as portable toilets found at worksites, and outdoor festivals, and on airplanes, railcars, recreational vehicles, boats, and buses. The aqueous composition may be visible to the person using the toilet, either because the receptacle is open to view or because the composition is recirculated for flushing a toilet bowl. In order to improve the appearance of the disinfectant composition containing accumulated waste, the composition typically includes a water-soluble or dispersable colorant, such as a blue dye.

A drawback of the present approach to coloring the disinfectant composition is that in order to effectively conceal accumulated waste, a relatively high concentration of colorant is required. The consequences of increasing the dye concentration are a greater likelihood of staining, higher cost and an additional burden on sewage treatment facilities, where it is often difficult to remove the color, even with secondary bleaching treatments. Watanabe, et al., U.S. Pat. No. 4,218,432, disclose use of certain polymethyne coloring agents in toilet bowl flushing water. The coloring agents of Watanabe et al. are decolorized by standard sewage treatment processes.

The use of opacifiers in liquid detergents, disinfectant shampoos and other cleaning products has heretofore been limited to enhancing the appearance of the cleaning composition itself. The opacifier does not serve a purpose when such compositions are employed in their intended use. For example, it is neither intended or desirable for the opacifier in a liquid soap to obscure the soil on ones hands during the washing process. Examples of compositions containing opacifiers may be found in the following United States patents: Fantl, U.S. Pat. No. 3,582,512; Carlson et al. U.S. Pat. No. 3,658,552; Widder et al. U.S. Pat. No. 4,009,139; Woodward et al. U.S. Pat. No. 4,597,975; Hirota et al. U.S. Pat. No. 4,717,501; and Richter et al. U.S. Pat. No. 5,336,500.

SUMMARY OF THE INVENTION

Therefore, one of the objects of the invention is to provide an aqueous composition for toilet receptacles with reduced light transmittance.

Another object of the invention is to provide a composition containing a low concentration of colorant.

Accordingly, a toilet system is provided having a receptacle for human waste which is partially filled with an aqueous composition, and preferably includes a disinfectant. The composition contains an opacifier, which is provided in sufficient concentration to reduce the light transmittance of the composition. Typically, the composition also incorporates a colorant and a perfume.

The invention has the advantage of using less colorant, while improving the aesthetics of the toilet system. In a preferred embodiment, the invention incorporates one or more of the following features:

a disinfectant;
the opacifier forms a stable dispersion in the composition at temperatures ranging from 0 to 50° C.;
a water-soluble colorant;
a composition suitable for use in closed systems; and
a composition which can provide an aesthetic liquor for flushing a toilet bowl, particularly a flushing liquor which can be recycled in a closed system.

DETAILED DESCRIPTION OF THE INVENTION

Without limiting the scope of the invention, the preferred embodiments and features are hereinafter set forth. Unless otherwise indicated, all parts and percentages are by weight, and conditions are ambient, i.e. one atmosphere of pressure and 25° C. The terms aryl and arylene are intended to be limited to single and fused double ring aromatic hydrocarbons. Unless otherwise specified aliphatic hydrocarbons are from 1 to 12 carbon atoms in length and cycloaliphatic hydrocarbons comprise from 3 to 8 carbon atoms.

The present invention includes a toilet system, which at a minimum, includes a receptacle for human waste (urine and feces). The receptacle is partially filled with an aqueous composition, which typically includes a disinfectant. The location, size and volume of the receptacle will vary depending upon the particular toilet system employed. For example, portable toilets, such as those found at construction sites and outdoor festivals, have a receptacle at their base and contain approximately 25 to 100 gallons of a disinfectant composition. Toilet systems found on airplanes and railcars typically employ a receptacle from which the disinfectant composition is drawn off and recycled to flush a toilet bowl.

The aforementioned systems are referred to herein as closed systems, in that the waste is temporarily stored in the receptacle in contact with the disinfectant composition. The receptacle is pumped out when the toilet system is periodically serviced, which may be after two hours or less of use, or as long as two or more days of use. Also within the scope of the present invention are toilet systems which discharge directly to sewage treatment systems, such as municipal plants and septic tanks, in which cases the receptacle containing the disinfectant composition is the toilet bowl itself, which can be supplied with the disinfectant composition from a dispenser in the toilet tank.

Conventional disinfectants may be employed in the aqueous composition of the present invention. The disinfectant functions to inhibit or kill micro-organisms in the toilet system, both for hygienic and aesthetic reasons. Compounds referred to in the art as antimicrobial agents, biocides, germicides, bactericides, fungicides, virucides, as well as bacteriostats and fungistats, are intended to be included within the scope of the term "disinfectant". By way of example, suitable disinfectants are disclosed in the *Kirk—Othmer Encyclopedia of Chemical Technology*, 4th Ed., "Disinfectants and Antiseptics", VoL 8, pages 237–292 (1993). Further examples of disinfectants which may be employed in the present invention may be found in Watanabe et al, U.S. Pat. No. 4,218,432; Woodard et al, U.S. Pat. No. 4,597,975; and Richter et al, U.S. Pat. No. 5,336,500. The concentration of disinfectant in the aqueous composition will vary, depending on the particular disinfectant compound(s) and toilet system employed. Generally, the disinfectant concentration ranges from 0.05 to 10 wt. % in the composition.

An opacifier is provided in the composition to increase light scattering resulting in reduced light transmittance. The overall reduction in light transmittance, which includes the effects of both light scattering and light absorbance, was evaluated using the following procedure:

The aqueous composition to be tested was added to a five gallon bucket, having a neutral gray interior. A 1½"×1" plastic coupon, either black or white and having a matte finish, was attached to a ruler and lowered into the composition. The depth at which the coupon was no longer visible was recorded. The measurement for the black and white coupon was averaged and reported as the "light transmittance." The observations were made under cool white fluorescent (CWF) light. A light transmittance of 10 inches or less is satisfactory; a light transmittance of 5 inches or less is preferred.

The concentration of opacifier needed to achieve the desired reduction in light transmittance will vary according to the particular opacifier employed, and generally will be between 0.1 ppm and 5 wt. %, preferably between 0.1 ppm and 1,000 ppm. Preferred opacifiers include those which form stable dispersions in aqueous compositions at temperatures ranging from 0 to 50° C. and pH ranges 2 to 11. By way of example, the following opacifiers may be employed:

A. Polymer latices, such as those formed by emulsion polymerization of styrene, butyl acrylate, butadiene, vinylidene chloride, methyl methacrylate, ethyl acrylate, methyl acrylate and acrylonitrile, and copolymers and terpolymers of such monomers. Such latices typically have a mean particle size of from 0.05 to 0.5 microns in diameter. Suitable latices are disclosed in Fantl, U.S. Pat. No. 3,582,512.

B. Dispersions of water insoluble, inorganic particulates, such as titanium dioxide. Suitable inorganic particulates are disclosed in Carlson et al, U.S. Pat. No. 3,658,552.

C. Emulsions of water insoluble, fatty acid glycol or glycerol esters, such as ethylene glycol distearate, hydrogenated coconut oil and mineral oil. Suitable compounds are disclosed in Carlson et al, U.S. Pat. No. 3,658,552, Hirota et al, U.S. Pat. No. 4,717,501 and Reng et al. U.S. Pat. No. 5,403,508.

D. Salts of long chain amines, such as disclosed in Dowell et al., U.S. Pat. No. 5,384,114.

E. Natural and synthetic gums and thickeners, such as gum arabic and hydroxymethyl cellulose.

A colorant may be provided to improve the aesthetics of the composition. The colorants are preferably water-soluble, however, colorants which form stable dispersions in aqueous liquor may also be used. By way of example, he colorant may be selected from water-soluble dyes, such as acid dyes, in particular Acid Blue 1 or Acid Blue 9, basic dyes, such as Methylene Blue, and poly(oxyalkylene) substituted colorants such as those disclosed in Kuhn, U.S. Pat. No. 3,157,633; Hauser et al, U.S. Pat. No. 4,144,028 and Brendle, U.S. Pat. No. 4,167,510, all incorporated by reference, and colorants sold under the Liquitint® trademark available from Milliken Chemical Division of Milliken & Company, Spartanburg, S.C. The colorants are included in the disinfectant composition in concentrations of from 0.1 ppm to 3 wt. %, preferably less than 3,000 ppm, most preferably, less than 100 ppm.

Miscellaneous other additives may be included in the disinfectant composition, including perfumes/deodorants, surfactants, chelating agents, and if the disinfectant composition is prepared from a solid or granule concentrate, various binders, fillers and extenders, as are well known in the art.

The viscosity of the composition at 25 C is generally less than 100 cp, preferably less than 20 cp.

The invention may be further understood by reference to the following examples, but the invention is not intended to be construed as being unduly limited thereby.

EXAMPLE 1

A five gallon bucket was filled with an aqueous composition having 5.6 ppm of a poly(oxyalkylene) substituted triphenylmethane colorant (Liquitint® Royal Blue) and 1.3 ppm solids of an acrylic—styrene emulsion polymer (Lytron® 44C). The light transmittance was measured and found to be 3.5 inches. A composition having 5.6 ppm of the colorant, but not the opacifier was also evaluated and found to have a light transmittance of greater than 10 inches.

EXAMPLE 2

A five gallon bucket was filled with an aqueous composition having 5.6 ppm of a poly(oxyalkylene) substituted triphenylmethane colorant (Liquitint ® Royal Blue) and 22 ppm of a gum arabic-glyeryl abietate dispersion (Neutral Cloud ®). The light transmittance was measured and found to be 3.5 inches. A composition having 5.6 ppm of the colorant, but not the opacifier was also evaluated and found to have a light transmittance greater than 10 inches.

EXAMPLE 3

A five gallon bucket was filled with an aqueous composition having 5.6 ppm of a poly(oxyalkylene) substituted triphenylmethane colorant (Liquitint® Royal Blue) and 79 ppm of an emulsified coconut oil. The light transmittance was measured and found to be 4.4 inches. A composition having 5.6 ppm of the colorant, but not the opacifier was also evaluated and found to have a light transmittance greater than 10 inches.

EXAMPLE 4

A five gallon bucket was filled with an aqueous composition having 5.6 ppm of a poly(oxyalkylene) substituted triphenylmethane colorant (Liquitint ® Royal Blue) and 48 ppm of emulsified limonene. The light transmittance was measured and found to be 3.2 inches. A composition having 5.6 ppm of the colorant, but not the opacifier was also evaluated and found to have a light transmittance greater than 10 inches.

EXAMPLE 5

A five gallon bucket was filled with an aqueous composition having 5.6 ppm of a poly(oxyalkylene) substituted triphenylmethane colorant (Liquitint ® Royal Blue) and 77 ppm of mineral oil dispersion. The light transmittance was measured and found to be 1.7 inches. A composition having 5.6 ppm of the colorant, but not the opacifier was also evaluated and found to have a light transmittance greater than 10 inches.

There are, of course, many alternate embodiments and modifications of the invention, which are intended to be included within the scope of the following claims.

What we claim is:

1. A toilet system comprising a toilet, a receptacle and an aqueous composition contained in the receptacle, the aqueous composition contains:
   (a) human waste selected from the group consisting of urine and feces;
   (b) from 0.1 ppm to 5 weight % of a light scattering opacifier, capable of reducing light transmittance, dispersed therein; and
   (c) from 0.1 ppm to 3 weight % of a water-soluble colorant dissolved therein.

2. The system of claim 1, wherein the aqueous composition further comprises a disinfectant in a concentration of from 0.05 to 10 weight %.

3. The system of claim 2, wherein from 25 to 100 gallons of the aqueous composition is contained in the receptacle.

4. The system of claim 1, wherein the water-soluble colorant is a poly(oxyalkylene) substituted colorant.

5. The system of claim 1 wherein the viscosity of the aqueous composition at 25° C. is less than 100 cp.

6. The system of claim 1, wherein the opacifier is a polymer latex.

7. The system of claim 1 wherein the viscosity of the aqueous composition at 25° C. is less than 20 cp.

8. A toilet system comprising a toilet, a receptacle and an aqueous composition contained in the receptacle, the aqueous composition contains:
   (a) human waste selected from the group consisting of urine and feces;
   (b) from 0.1 ppm to 1,000 ppm of a light scattering opacifier, capable of reducing light transmittance, dispersed therein, wherein the opacifier is selected from the group consisting of polymer latices, dispersions of inorganic particulates, emulsions of fatty acid glycol and glycerol esters, hydrogenated coconut oil, mineral oil salts of long chain amines and natural and synthetic gums and thickeners;
   (c) from 0.1 ppm to 3,000 ppm of a water-soluble colorant dissolved therein; and
   (d) from 0.5 to 10 weight % of a disinfectant.

9. The system of claim 8, wherein from 25 to 100 gallons of the aqueous composition is contained in the receptacle.

10. The system of claim 8 wherein the water-soluble colorant is a poly(oxyalkylene) substituted colorant.

11. The system of claim 8 wherein the viscosity of the aqueous composition at 25° C. is less than 100 cp.

12. The system of claim 8 wherein the viscosity of the aqueous composition at 25° C. is less than 20 cp.

* * * * *